United States Patent

Amundson et al.

Patent Number: 5,324,261
Date of Patent: Jun. 28, 1994

[54] DRUG DELIVERY BALLOON CATHETER WITH LINE OF WEAKNESS

[75] Inventors: Rodney R. Amundson, Lindstrom; Vincent W. Hull, Ham Lake; Michael Dror, Edina; Robert S. Schwartz, Rochester, all of Minn.

[73] Assignee: Medtronic, Inc., Minneapolis, Minn.

[21] Appl. No.: 989,412

[22] Filed: Dec. 11, 1992

Related U.S. Application Data

[63] Continuation-in-part of Ser. No. 853,661, Mar. 19, 1992, which is a continuation-in-part of Ser. No. 637,436, Jan. 4, 1991, Pat. No. 5,102,402.

[51] Int. Cl.⁵ .......................................... A61M 29/00
[52] U.S. Cl. ...................................... 604/96; 604/265
[58] Field of Search .............. 604/265, 266, 96, 101, 604/52, 53; 606/192, 194

[56] References Cited

U.S. PATENT DOCUMENTS

| | | | |
|---|---|---|---|
| Re. 31,873 | 4/1985 | Howes | 604/21 |
| 3,086,525 | 4/1963 | Whitcomb . | |
| 3,169,527 | 2/1965 | Sheridan . | |
| 3,817,248 | 6/1974 | Buckles . | |
| 3,885,561 | 5/1975 | Cami . | |
| 3,971,385 | 7/1976 | Corbett . | |
| 4,417,576 | 11/1983 | Baran | 604/101 |
| 4,423,725 | 1/1984 | Baran . | |
| 4,437,856 | 3/1984 | Valli | 604/29 |
| 4,603,152 | 7/1986 | Laurin | 604/265 |
| 4,655,746 | 4/1987 | Daniels | 604/53 |
| 4,710,181 | 12/1987 | Fuqua | 604/265 |
| 4,714,460 | 12/1987 | Calderon | 604/28 |
| 4,717,379 | 1/1988 | Ekholmer | 604/43 |
| 4,769,013 | 9/1988 | Lorenz | 604/265 |
| 4,784,647 | 11/1988 | Gross | 604/178 |
| 4,790,813 | 12/1988 | Kensey | 604/23 |
| 4,839,175 | 6/1989 | Guo | 424/450 |
| 4,900,303 | 2/1990 | Lemelson | 604/54 |
| 4,913,683 | 4/1990 | Gregory | 604/8 |
| 4,923,450 | 5/1990 | Maeda | 604/265 |
| 4,968,307 | 11/1990 | Dake | 604/264 |
| 4,994,033 | 2/1991 | Shockey et al. | 604/101 |
| 5,015,231 | 5/1991 | Keith | 604/96 |
| 5,049,130 | 9/1991 | Powell | 604/96 |
| 5,049,132 | 9/1991 | Shaffer | 604/101 |
| 5,078,681 | 1/1992 | Kawashima | 604/96 |
| 5,087,244 | 2/1992 | Wolinsky et al. | 604/53 |
| 5,092,841 | 3/1992 | Spears | 604/96 |
| 5,098,381 | 3/1992 | Schneider | 604/96 |
| 5,103,817 | 4/1992 | Reisdorf et al. | 604/100 |
| 5,112,305 | 5/1992 | Barath | 604/96 |

FOREIGN PATENT DOCUMENTS 54-35036 10/1979 Japan .
8912478 6/1988 World Int. Prop. O. .

OTHER PUBLICATIONS

"Direct Intraarterial Wall Injection of Microparticles via a Catheter: A Potential Drug Delivery Strategy Following Angioplasty" by Wilensky et al. in Progress in Cardiology, Oct. 1991.

Primary Examiner—Jerome L. Kruter
Attorney, Agent, or Firm—Daniel W. Latham; Harold R. Patton

[57] ABSTRACT

A balloon catheter includes a sheath surrounding the balloon, the sheath having a longitudinal line of weakness and a drug-containing viscous matrix material intermediate between the balloon and the sheath such that when the balloon is positioned and inflated in the body lumen it causes the sheath to burst at the line of weakness and release viscous matrix material onto said body lumen. The device provides accurate placement of the dosage required at the location in need of treatment. The catheter is especially useful in balloon angioplasty procedures.

9 Claims, 3 Drawing Sheets

DRUG DELIVERY BALLOON CATHETER WITH LINE OF WEAKNESS

This application is a continuation-in-part of U.S. Ser. No. 07/853,661 filed Mar. 19, 1992 pending which is a continuation-in-part of U.S. Ser. No. 07/637,436 filed Jan. 4, 1991, now U.S. Pat. No. 5,102,402 .

BACKGROUND OF THE INVENTION

This invention relates to balloon catheters and more particularly to balloon angioplasty catheters having therapeutic compounds releasably attached to a balloon.

Dilatation balloons on catheters are well known in the art and are used to decrease the restriction caused by plaque within a vessel wall. Plaque varies greatly in consistency and may be anything from a soft fatty tissue to a harder calcified material. In either case, it is often desirable to do more than simply force a balloon against the plaque or other restriction in the hopes that any plaque and vessel wall may be stretched to open the lumen more fully. Laser angioplasty uses lasers to vaporize the plaque at the stenosis, while atherectomy uses cutting actions to remove the plaque.

Researchers are currently screening a number of drugs to limit or dissolve plaque and to limit the growth of neointimal tissue. Unfortunately, such compositions have been difficult to apply directly where needed. Instead, such drugs tend to be applied systemically which essentially treats portions of the body which need no treatment. Also, such treatments mean that the dosage to the body must be quite high to insure that the localized area having a need for treatment will receive adequate drugs.

Concentrated heparin is delivered by a perforated balloon catheter in work by Wolinsky et al, as described in European Patent publication 0 383 429 of C. R. Bard, Inc. The drug is sprayed through minute holes in the balloon. Also see JACC Vol. 15, No. 2, February 1990:475-81 by Wolinsky et al.

The assignee of the present invention has filed a patent application entitled "Intraluminal Drug Eluting Prosthesis", Serial No. 07/486,580, filed Feb. 28, 1990 which places a stent bearing drug at the location desired. Other attempts have involved an application of catheters having separated balloons and the introduction of the drug from an internal lumen of the catheter to the space formed between two inflated balloons. Obviously, this procedure requires the introduction of drug through a lumen within the catheter meaning that the volume of the drug is quite high. Also, if the plaque is badly fissured there will not be a complete seal between the two balloons and the drug will escape to other parts of the body through the vessel. Also, the time available for treatment with such a system is quite short since the balloons must eventually be deflated to allow blood to flow.

SUMMARY OF THE INVENTION

We have discovered a method and apparatus for placing therapeutic substances such as plaque-affecting drugs, blood affecting drugs or diagnostic materials where it is needed in a blood vessel or other body lumen by the use of a sheath containing a drug-loaded viscous matrix material which is placed over the balloon of a balloon catheter. When delivered to the point of treatment and the balloon is inflated, the sheath bursts along a longitudinal line of weakness to deliver the viscous matrix material to the surface of the body lumen. The invention allows the modification of any existing balloon catheter by applying the sheath and drug-containing viscous matrix material to the exterior of a balloon. The drug may be applied to the balloon in the form of microcapsules, polymer coated crystals, or other drug forms which may be incorporated in a viscous matrix. The term "drug" as used herein refers to any agent or combination of agents that may affect the cells in the lumen or blood, or artery wall and includes diagnostic reagents.

Generally, the drug or other bioaffecting chemical is placed in a viscous matrix material which may be coated over the balloon. When delivered to the site of a plaque-containing occlusion or stenosis in a blood vessel, the viscous matrix and included drug can come into intimate contact with the plaque or vessel wall and fill any fissures which may be present in the plaque. The drug in highly concentrated form is therefore placed exactly where it is needed and then sticks to the wall of the lumen. The actual dosage is extremely small since it must only affect the intended region.

The invention allows a physician to determine the type and extent of the plaque and then either use a catheter already loaded with a drug-containing viscous matrix material or to coat a catheter with a drug-containing viscous matrix as desired at the dosage indicated and apply a sheath with a longitudinal line of weakness over the viscous matrix material to protect the viscous matrix material as it is inserted. The balloon may be substantially the same as existing angioplasty balloons.

DETAILED DESCRIPTION OF THE INVENTION

Figure 1:
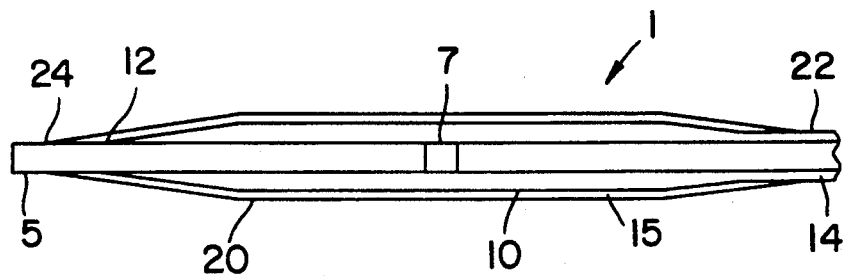
FIG. 1 is a longitudinal sectional view of the balloon portion of an uninflated balloon catheter with viscous matrix material and sheath according to the invention.

The drugs in the viscous matrix may be of any type which would be useful in treating the artery or lumen. By treatment, the invention also contemplates diagnostic techniques which will aid in later treatment. Thus "drugs" may include diagnostic agents such as radiopaque compounds that allow the vessel to be visualized by fluoroscopy or similar methods. A dye within the viscous matrix would be visible on the plaque after release by fluoroscopy.

In order to prevent restenosis in blood vessels, migration and subsequent proliferation of smooth muscle cells must be checked. Platelet aggregation and adhesion and thrombus formation can be controlled with antiplatelet agents, fibrinolytics, anticoagulants or anti-thrombotics. Growth factor and receptor blockers and antagonists may be used to limit the normal repair response. The drugs may be in a liquid, semi-liquid or crystalline form. If crystalline, the crystals, coated or uncoated, may function as microcapsules and be adhered to the balloon wall by the viscous matrix material.

Microcapsules may be used to control delivery of drugs in the viscous matrix material. Microcapsules usable in the present invention may be fabricated in accordance with any of the known methods for preparing microcapsules. U.S. Pat. Nos. 4,897,268, 4,675,189, 4,542,025, 4,530,840, 4,389,330, 4,622,244, 4,464,317 and 4,943,449, the disclosures of which are incorporated herein by reference, describe methods for forming microcapsules which would be suitable for this invention. Microencapsulation is also described in *Encyclopedia of Poly. Sci. & Eng,* Vol. 9, by Curt Thies at pages 724–745 (2nd Ed. 1985) and in a chapter on Microencapsulation by R. E. Sparks in Kirk-Othmer, pages 470–493, Vol. 15 (3rd Ed).

The microcapsules may either be rupturable to release their contents or may be degradable such that they will provide slow drug release when left against the lumen walls. The capsules may release their contents through diffusion or by rupturing due to the application of ultrasonic forces. Many of the current applications for microcapsules require them to be easily ruptured under pressure, as in the case of carbonless copy paper. Typically, the microcapsules would be on the order of from 2 to 100 microns in diameter. The drug within the microcapsule will typically be in solution or otherwise dispersed throughout the polymer of the microcapsule. However, since it is possible to microencapsulate crystals, drug crystals may be employed. In such cases, the microcapsule may present sharp angles which will easily become embedded and fixed to the artery wall when the balloon is inflated.

When referred to herein, "microcapsule" shall include microspheres. The release mechanisms from the microcapsules may include any of the existing release mechanisms, such as those described by Robert Langer in "New Methods of Drug Delivery", *Science,* Vol. 249, 28 Sep. 1990, pp. 1527:1533.

The viscous matrix material of the present invention can be any viscous, tacky material which is biocompatible and may be bioabsorbable or bioerodeable and which provides a chemically compatible carrier for the chosen drugs or drug-containing microcapsule. Bioabsorbable waxes, pastes or gels could be made from materials such as polyvinyl pyrrolidone, proteins (e.g., albumin, fibrinogen fibrin, gelatin), fats, carbohydrates (e.g., dextran, sucrose, cellulose, hyaluronic acid), low molecular weight bioabsorbable polymers, copolymers and water soluble pastes, (e.g., polyglycolic acid, polylactic acid, polyorthoesters, polyphosphoesters). A plasticizer/solubilization agent such as glycerol, propylene glycol, or sorbitol can also be used in the viscous matrix. The viscosity of the viscous matrix material should be in the range of about 1–10,000 poise and preferably in the range of about 10–3000 poise.

Suitable viscous matrix materials have been disclosed in the following U.S. patents which are incorporated herein by reference. In U.S. Pat. No. 5,030,457 issued to Heller et al., bioerodable orthoester polymers in the form of ointment, creams, gels and the like may incorporate pharmaceutical compositions for administration to a patient. The drug release rate and delivery time can be modified as disclosed therein. In U.S. Pat. No. 4,994,277, issued to Higham et al., a viscoelastic, bioerodable gel made from Xanthan gum is disclosed for use in the prevention of adhesions with the rate of breakdown in the body adjustable according to the concentration of Xanthan gum. In U.S. Pat. No. 4,898,734 issued to Mathiowitz et al., a composite material is disclosed in which microcapsules or microspheres are embedded in a continuous polymeric matrix. The microcapsules and microspheres are made from polymers such as polyanhydrides, polyorthoesters, polystyrene, polyurethane, polypropylene, polymethacrylate, polyglycolic acid, and polylactic acid. In U.S. Pat. No. 4,818,517 issued to Kwee et al., a viscous pharmaceutical preparation is disclosed for injection into a body cavity in which a swellable hydrogel (e.g., crosslinked polymers of starch, dextran, insulin, polyvinyl alcohol, dextrin, sorbitol) is used as a carrier for placement of drugs into the body cavity. In U.S. Pat. No. 4,612,009 issued to Drobnik et al., a biodegradable gel implant is disclosed in which a starch gel incorporates an antitumor agent for implantation in the human body.

The viscous matrix can be combined with drugs as set forth herein by including the drugs in microcapsules and incorporating the microcapsules into the viscous matrix. Alternatively, the drugs can be incorporated directly into the viscous matrix without the use of microcapsules.

The balloon catheters of the invention may include any balloon catheter to which a viscous matrix and sheath may be applied. The catheter need not be a dilation catheter as such. Any balloon catheter, whether capable of use in angioplasty or not may be employed. Since much lower pressures may be needed to release the drug, the balloon may be formed from an elastomer rather than a polyethylene or other high pressure balloon material.

In conventional balloon angioplasty, a balloon catheter is inserted into the cardiovascular system until the balloon is located at an occlusion site. The balloon is then inflated by the addition of pressurized fluid which unfolds the balloon presenting a relatively smooth outer surface or working profile for exerting radially outward forces on the plaque. This accomplishes vessel dilation which reduces the degree of occlusion by the plaque.

In the present invention, the same balloon catheter may also be used to apply drugs or other agents directly to the vessel wall where needed. The viscous matrix which carries the active agents is placed directly against the plaque or other tissue of the vessel wall inflating the balloon. The viscous matrix may then release the incorporated drugs to the occluded vessel. Where intimal flaps are present, the invention allows the placement of a large portion of the viscous matrix within the fissures that are normally difficult to reach and treat, and are often the source of subsequent hyperplasia.

To protect the viscous matrix from being rubbed off of the balloon during the movement of the viscous matrix coated balloon through the body lumen, a protective sheath is applied over the balloon and viscous matrix. The sheath has at least one longitudinal line of weakness which allows the sheath to burst as the balloon is inflated, thereby releasing the viscous matrix material onto the lumen. The sheath could be made of many polymeric materials known to be suitable for use in catheters so long as the selected sheath material will split longitudinally to allow the viscous matrix material to be applied. For example, silicone rubber and latex rubber could be used. Preferably, the sheath material is an elastomeric material which will also spring back when it splits to expose more of the body lumen to the viscous matrix material. For example, a thin, extruded silicone tube (SSF-MEXD-516 - 70 durometer) having a wall thickness of about 0.003 inches could be used. The line of weakness could be provided by scoring or perforating the sheath material although the extrusion or longitudinal stretching of the material can be sufficient to provide longitudinal orientation of the polymer and therefore lines of longitudinal weakness as contemplated in this invention. Therefore the extruded silicone tube described above need not be provided with perforation or scoring when used in the present invention. However, if additional control over the timing of viscous matrix delivery or of placement of the viscous matrix material is desired, the tube could be scored or perforated to the extent desired. The tube is preferably made with an internal dimension approximating the outside dimension of the uninflated balloon. The silicone tube can then be expanded and placed over the balloon and also over the viscous matrix material that has been previously placed on the balloon. The expansion of the tube can be accomplished, for example, by mechanical means or by immersing the tubing in a suitable solvent and allowing the tubing to swell and expand. Preferred solvents are those which are substantially biocompatible such as the fluorocarbon solvents sold under the tradename FREON. The solvent-expanded tube could then be placed over the balloon and viscous matrix material. Once the solvent evaporates, the tube will return to its original size and will fit tightly about the balloon and viscous matrix material. Mechanical expansion of the tubing can also be accomplished by placing the silicone tubing over a separate balloon and dilating the balloon to the extent needed to make tubing large enough to clear the balloon and viscous matrix material on the catheter. The balloon is then deflated and the tubing is placed over the balloon and viscous matrix material. The tubing then returns to its usual diameter and provides a good fit over the balloon and viscous matrix material. When the balloon with viscous matrix material is later expanded, the sheath is expanded to the extent that it exceeds its elastic limit at the line of weakness and bursts to expose and therefore deliver the viscous matrix material to the body lumen.

When the tubing is seated over the balloon and matrix material, it is preferable sealed at each end to prevent the viscous matrix material from being forced from the ends of the tubing before the sheath bursts. Sealing can be accomplished by methods conventionally used to bond polymeric catheter components such as, for example, solvent bonding, medical adhesives, epoxies or UV-cure adhesives. However, preferably no adhesive is applied, rather relying on the fit between the I.D. of the sheath and the O.D. of the catheter shaft and tip.

Figure 2:
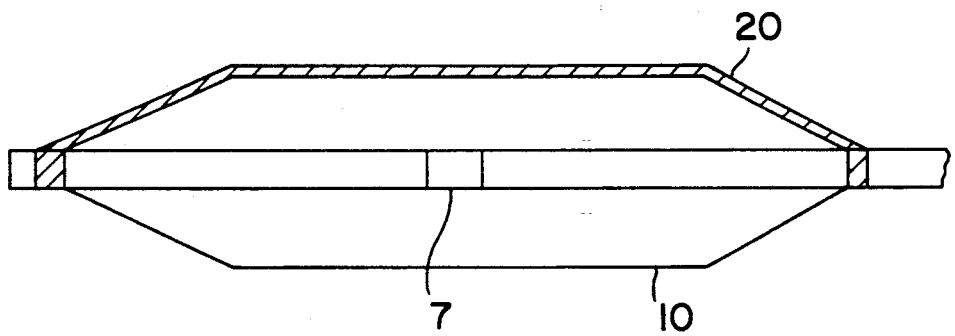
FIG. 2 is the same view as FIG. 1 of the catheter of FIG. 1 showing the balloon inflated and the sheath burst.
Figure 3:
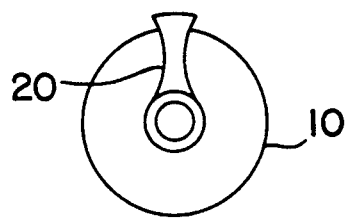
FIG. 3 is an end elevational view of the catheter of FIG. 2 with inflated balloon and burst sheath.
Figure 4:
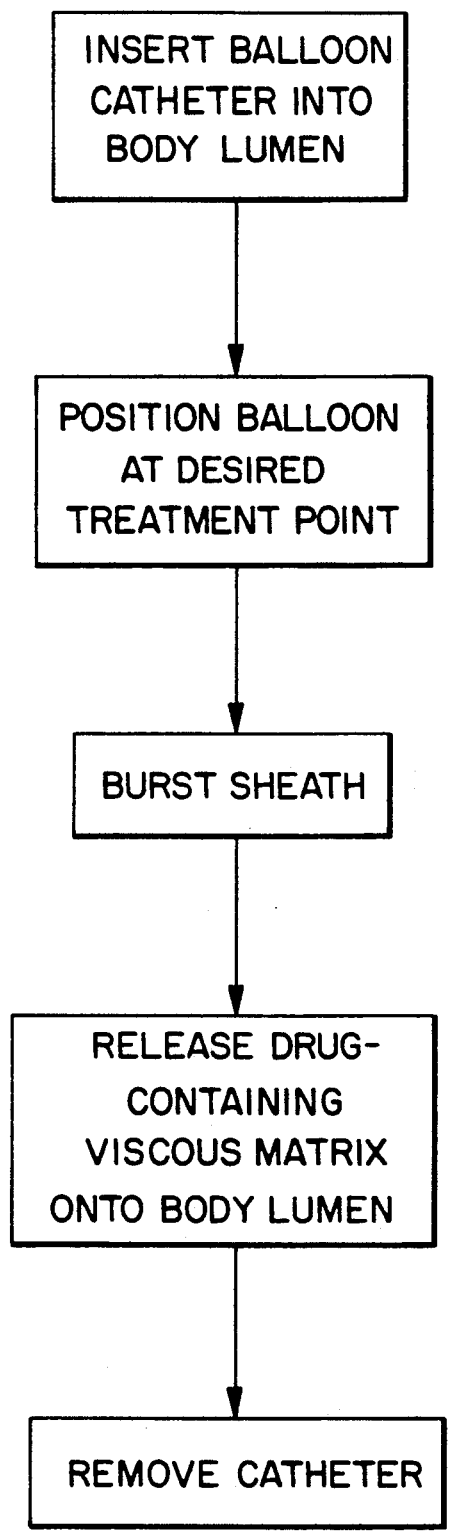
FIG. 4 is a flow diagram of the method of treatment according to the present invention.
Figure 5:
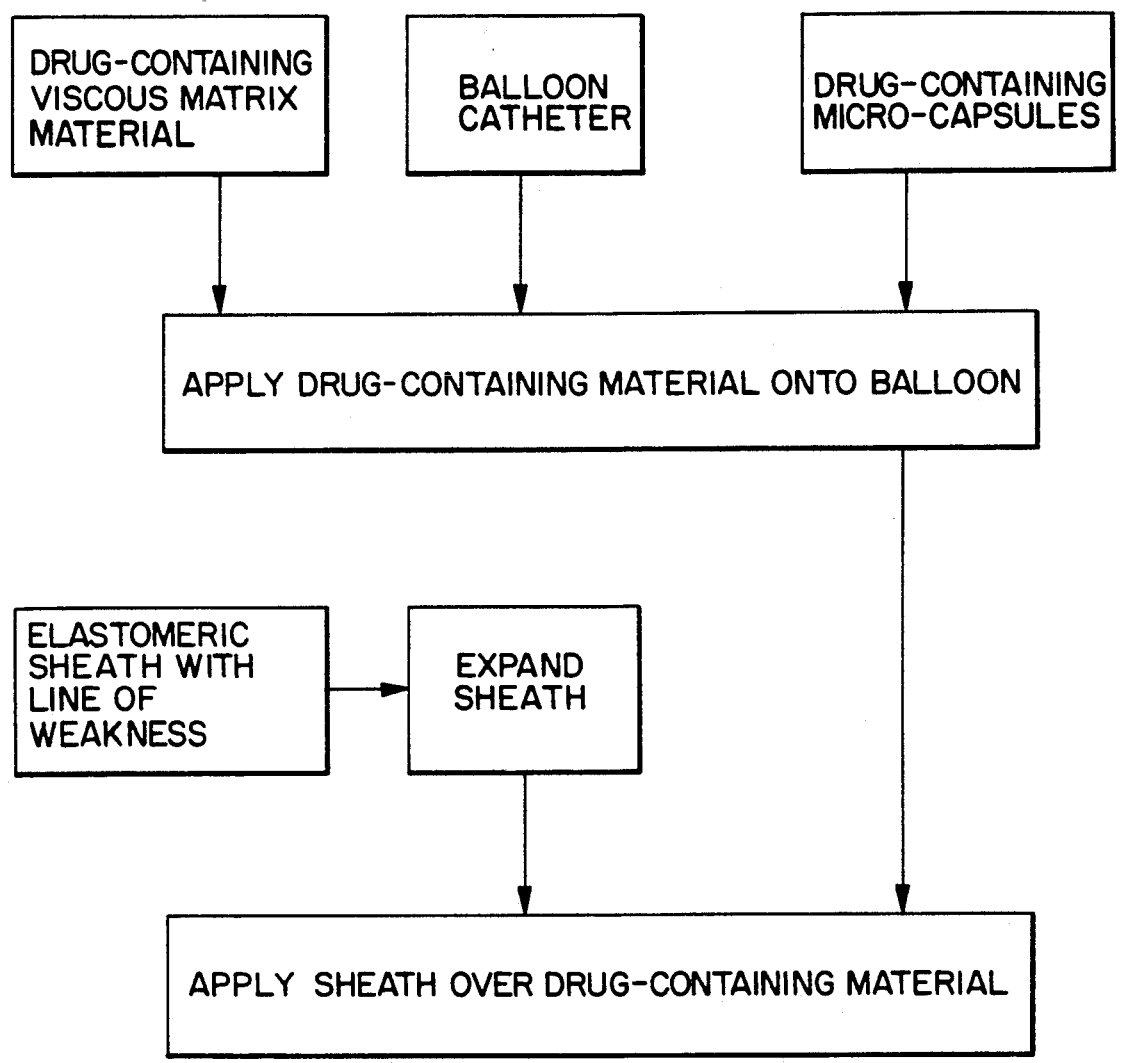
FIG. 5 is a flow diagram of a method of making the device according to the present invention.

Referring now to FIGS. 1-3, FIG. 1 shows the balloon portion of a catheter 1 made according to the present invention which includes a catheter shaft 5 including a marker band 7 of radio-opaque material which allows for the correct positioning of the balloon portion of the catheter 1 in the body lumen (not shown). Surrounding the shaft 5 is a balloon 10 shown in a deflated condition, the balloon 10 having a seal 12 to the shaft at a distal end and having a passageway 14 at a proximal end which allows the balloon to be inflated. Surrounding the balloon 10 is a viscous matrix material 15 containing a drug and a sheath 20 which confines the viscous matrix material 15 to the annular space between the balloon 10 and sheath 20. To prevent the viscous matrix material 15 from being squeezed out at the ends of the sheath 20 as the balloon 10 is expanded, seals 22, 24 are provided at the proximal and distal ends. FIG. 2 shows the catheter 1 of FIG. 1 with the balloon 10 in an expanded state. Expansion of the balloon 10 has caused the sheath 20 to burst along a longitudinal line of weakness (not shown) created by the longitudinal orientation of the sheath material when it was originally-extruded as tubing. Due to its elastomeric nature, the burst sheath 20 contracts or folds to one side of the balloon 10, thereby allowing the viscous matrix material (not shown) to be exposed and therefore delivered to substantially the entire circumference of the body lumen. This orientation of the burst sheath 20 and expanded balloon 10 is shown more fully in FIG. 3.

The dilatation catheters of the invention are used according to well known catheterization procedures. However, due to the presence of the viscous matrix material when the balloon is inflated the viscous matrix material and the drugs contained therewithin are delivered to the lumen wall, especially to any fissured areas at the site being treated.

The amount of drug needed to treat the cells at a specific site in a vessel lumen is quite small. The viscous matrix material can easily carry the amount of cell affecting agents to the treatment site. A lower dosage is thus possible by the invention as well as a means to limit the possibly undesired side effects of the drug on other areas of the body.

While this invention may be embodied in many different forms, they are shown in the drawings and described in detail herein specific preferred embodiments of the invention. The present disclosure is an exemplification of the principles of the invention and is not intended to limit the invention to the particular embodiments illustrated. Those skilled in the art may recognize other equivalents to the specific embodiment described herein which equivalents are intended to be encompassed by the claimed attached herein.

We claim:

1. In a catheter of the type comprising a catheter body and an inflatable balloon positioned along the length of the catheter body; the improvement comprising:

a sheath over the balloon, the sheath having a longitudinal line of weakness sufficient to cause the sheath to burst at the line of weakness as the balloon is inflated; and a viscous matrix material intermediate between the balloon and the sheath, said viscous matrix material having a drug or combination of drugs for treatment or diagnostics within a body lumen such that when the balloon is inflated it causes the sheath to burst at the line of weakness and expose the viscous matrix material.

2. The catheter of claim 1 wherein said viscous matrix also includes drug-containing microcapsules.

3. The catheter of claim 1 wherein said viscous matrix has anti-restenosis drugs therein.

4. The catheter of claim 1 wherein said viscous matrix comprises a bioabsorbable polymer selected from the group consisting of polyorthoester, polysaccharide, polyphosphoester, polyglycolic acid, polylactic acid and polyvinyl pyrrolidone.

5. The catheter of claim 1 wherein said viscous matrix material is sealed within the sheath.

6. The catheter of claim 5 wherein the sheath is sealed at its proximal and distal ends to the catheter.

7. The catheter of claim 1 wherein the sheath is made from an elastomeric material.

8. The catheter of claim 7 wherein the elastomeric material is a silicone elastomer.

9. A method for applying a drug to a body lumen comprising the steps of:
   a. inserting a dilatation catheter having a drug-containing viscous matrix material on the exterior of a catheter balloon and a sheath having a longitudinal line of weakness over the balloon and viscous matrix material into a body lumen to a point where treatment is desired;
   b. bursting the sheath at the line of weakness by expanding said balloon, thereby exposing the viscous matrix material;
   c. releasing the exposed viscous matrix material against the lumen wall; and
   d. removing said dilatation catheter.